US00PP36380P2

(12) United States Plant Patent
Meilland

(10) Patent No.: US PP36,380 P2
(45) Date of Patent: Jan. 14, 2025

(54) HYBRID TEA ROSE PLANT NAMED 'MEILEHAGAN'

(50) Latin Name: *Rosa hybrida*
Varietal Denomination: MEILEHAGAN

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/615,373

(22) Filed: Mar. 25, 2024

(30) Foreign Application Priority Data

Feb. 2, 2024 (QZ) ..... PBR 2024/0308

(51) Int. Cl.
*A01H 5/02* (2018.01)
*A01H 6/74* (2018.01)

(52) U.S. Cl.
USPC ..... Plt./138
CPC ..... *A01H 6/749* (2018.05)

(58) Field of Classification Search
USPC ..... Plt./138
CPC ..... A01H 6/749; A01H 5/02
See application file for complete search history.

(56) References Cited

U.S. PATENT DOCUMENTS

| | | | |
|---|---|---|---|
| PP6,895 | P | 7/1989 | Meilland |
| PP8,617 | P | 3/1994 | Kordes |
| PP11,660 | P | 11/2000 | Meilland |

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEILEHAGAN', is described. The new variety is a hybrid tea rose plant. The new variety forms in abundance on a substantially continuous pink colored blossom which are peony shaped. Dense, dark green foliage with a glossy aspect is exhibited.

1 Drawing Sheet

Latin name of genus and species of plant claimed: *Rosa hybrida.*

Variety denomination: 'MEILEHAGAN'.

CROSS REFERENCE TO RELATED APPLICATIONS

This application claims priority to Plant Breeders' Right Application No. 2024/0308, which was filed at Community Plant Variety Office in the European Union on Feb. 2, 2024, the contents of which are hereby incorporated by reference for all purposes.

STATEMENT REGARDING PRIOR DISCLOSURES BY THE INVENTOR

The first sale or offer for sale of the new variety was Mar. 31, 2023, in France. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding in Le Cannet des Maures, Var, France by artificial pollination wherein two parents were crossed which previously had been studied in the hope that they would contribute the desired characteristics. The female parent (i.e., the seed parent) of the new variety was an unnamed seedling, which was the product of the cross between 'MEIVILDO' (U.S. Plant Pat. No. 6,895) and 'DORIS TYSTERMAN' (not patented). The male parent (i.e., the pollen parent) of the new variety was an unnamed seedling, which was the product of the cross between 'KORBACOL' (U.S. Plant Pat. No. 8,617) and an unnamed seedling.

The parentage of the new variety can be summarized as follows: ('MEIVILDO' x DORIS TYSTERMAN') x ('KORBACOL' x unnamed seedling).

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms elegant peony shaped blossoms, (b) displays pink colored flowers, and (c) exhibits dark green colored glossy foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the seed parent displays cream grey colored flowers compared to the pink-colored flowers of the new variety. Additionally, the pollen parent displays orange-colored flowers compared to the pink colored flowers of the new variety. Moreover, the new variety can be readily distinguished from non-parental related similar varieties. For example, the 'MEIZINCARO' variety (U.S. Plant Pat. No. 11,660) displays cardinal red colored blossoms compared to the pink colored blossoms of the new variety.

The new variety has been named the 'MEILEHAGAN' variety.

BRIEF DESCRIPTION OF THE PHOTOGRAPHS

The accompanying photograph shows, as nearly true as it is reasonably possible to make the same in a color illustration of this character, typical specimens of the plant parts of the new variety. The rose plants of the new variety were approximately three years of age and were observed during March while budded on their own roots and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical feature. The description is based on a three-year-old specimen of the new variety, observed during March, while budded on its own roots and growing outdoors at Le Cannet des Maures, Var, France.

Botanical classification: *Rosa hybrida* cultivar 'MEILEHAGAN'.

Commercial classification: Hybrid Tea Rose Plant.

Plant:

*Habit*.—Bushy and compact.

*Height*.—Approximately 100.0 cm on average.

*Width*.—Approximately 100.0 cm on average.

Branches:

*Stem color*.—Young stems: Green Group 137D more or less suffused with Greyed-Purple Group 187D. Adult wood: Green Group 137B more or less suffused with a color in between Greyed-Purple Group 187D and Brown Group 200A and on old wood streaked with Greyed-Orange Group 165B.

*Length*.—From the crown to the flower is typically between 20 to 60 cm.

*Diameter*.—Typically between 0.6 cm to 1.2 cm.

*Thorns*.—Configuration on adult stems: upright to slightly concave, elongated and curved downwards on the upper surface and very concave on the under surface. Long prickles — quantity: approximately 13 thorns on average per 10 cm long young stem and approximately 8 thorns on average per 10 cm long adult stem. Long prickles — length: typically between 0.5 cm to 0.7 cm on young stems and on adult stems. Long prickles — width at base: typically between 0.1 cm to 0.2 cm on young stems and typically between 0.3 cm and 0.4 cm on adult stems. Long prickles — base shape: obovate, broad, and short on young stems; obovate, broad, and rather short on adult stems. Long prickles — color on young stems: Red-Purple Group 60A. Long prickles — color on adult stems: a color between Greyed-Orange Group 165A and Greyed-Orange Group 165B. Small prickles — quantity: approximately 5 thorns on average per 10 cm long young stem and approximately 60 thorns on average per 10 cm long adult stem. Small prickles — length: typically between 0.1 cm to 0.3 cm on young stems and on adult stems. Small prickles — width at base: approximately 0.1 cm on average on young stems and on adult stems. Small prickles — base shape: obovate on adult stems. Small prickles — color on young stems: Red-Purple Group 60B. Small prickles — color on adult stems: a color between Greyed-Orange Group 165A and Greyed-Orange Group 165B.

*Anthocyanin coloration of young shoots*.—Greyed-Purple Group 184A.

*Internode numbers on entire branch*.—Typically between 7 to 15.

*Internode length*.—Typically between 2.5 to 5.0 cm.

Leaflets:

*Number*.—3, 5, 7; most often 5.

*Shape*.—Tip: attenuated. Base: rounded.

*Serration*.—Small and single.

*General appearance*.—Oval.

*Undulation*.—Very weak.

*Glossiness of upper side*.—Strong.

*Texture*.—Moderately leathery.

*Smoothness*.—Upper surface: smooth. Under surface: smooth.

*Venation*.—Color is Green Group 138C; and pattern is imparipinnate.

*Size*.—Terminal leaflet: length is typically between 5.7 cm to 7.5 cm; width is typically between 3.8 cm to 4.0 cm. 5-leaflet leaf: length is typically between 12.0 cm to 16.0 cm; width is typically between 9.0 cm to 10.0 cm.

Foliage:

*General appearance*.—Dense, darker with a glossy aspect.

*New foliage*.—Upper surface color: a color between Green Group 137A and Green Group 139A. Under surface color: Green Group 137A strongly covered with Greyed-Purple Group 184A.

*Adult foliage*.—Upper surface color: Green Group 137A. Under surface color: Green Group 137A more or less suffused with Greyed-Purple Group 187A.

*Petiole*.—Texture: upper surface is glandular; under surface is smooth. Length: typically between 1.3 to 3.0 cm. Width: typically between 0.1 to 0.2 cm. Upper surface color: Green Group 137A. Under surface color: Green Group 137D.

*Rachis*.—Rachis length of terminal leaflet: typically between 4.5 to 6.5 cm. Rachis width of terminal leaflet: typically between 0.1 to 0.2 cm. Texture: upper surface is glandular; under surface is smooth. Upper surface color: Green Group 137A. Under surface color: Green Group 138D.

*Stipules*.—Length: typically between 1.5 cm to 2.2 cm. Width: typically between 0.3 cm to 0.4 cm. General appearance: moderately broad. Texture: smooth on upper and under surfaces. Upper surface color: Green Group 137A slightly suffused with Greyed-Purple Group 187A. Under surface color: Green Group 137D.

Inflorescence:

*Number of flowers per stem*.—Typically between 1 to 5 flowers per stem.

*Lastingness of the bloom*.—On the plant: approximately 7 days. In vase: not tested.

*Bud*.—Shape: globular. Length: typically between 2.5 cm to 3.5 cm. Width: typically between 2.0 cm to 2.5 cm. Color as calyx breaks: Upper surface: petals of the external rows are a color between Red-Purple Group 67A and Red-Purple Group 66A; all other more internal petals are Red-Purple Group 67A; basal spot is Yellow Group 8C. Under surface: petals of the external rows are Red-Purple Group 67A; all other more internal petals are Red-Purple Group 67B; basal spot is Yellow Group 8D.

*Sepals*.—Number: commonly 5. Length: approximately 2.8 cm on average. Width: approximately 1.0 cm on average. Shape: At the top: elongated and moderately large. At the base: flat at union with the receptacle. Extensions: typically 2 sepals with strong extensions, 1 sepal with medium extension, and 2 sepals with weak extensions or without extension. Upper surface: Texture: tomentous. Color: Yellow-Green Group 144A covered with hairs near White Group 155B. Under surface: Texture: slightly tomentous and glandular on board. Color: Yellow-Green Group 144A slightly suffused with Green Group 143A.

*Receptacle*.—Color: Yellow-Green Group 144A. Length: approximately 1.0 cm on average. Surface: smooth. Shape: pitcher shaped.

*Peduncle*.—Length: approximately 6.0 cm on average. Width: typically 0.3 cm to 0.5 cm. Surface: glandular. Color: Yellow-Green Group 144A.

*Flower*.—Diameter when open: approximately 10 cm on average. Depth of the flower: typically between 4.0 cm to 5.0 cm. Shape: cup shaped. Shape when viewed from above: irregular rounded. Shape of the upper part of the flower profile: flattened convex. Shape of the lower part of the flower profile: flat. Type: very double. Number of petals under normal conditions: typically between 60 and 65. Petals: Shape: rounded (rounded slightly acuminate at the top and acute at the base). Texture: thick and soft. Length: typically between 3.5 cm to 4.5 cm. Width: typically between 2.5 cm to 3.5 cm. Undulation of the petal: weak. Reflexing of the petal: very weak. Petal incision: strong. Petal arrangement: imbricated with few petaloids (few and crumpled half petal). Petal drop: petals drop off cleanly before drying. Fragrance: very slight (green/fresh). Discoloration of the flower: very slight. Color when opening: Basal spot on the upper surface: Yellow Group 8C. Upper surface: petals of the external rows are a color between Red-Purple Group 66A and Red-Purple Group 67A; all other more internal petals are Red-Purple Group 67C. Basal spot on the under surface: Yellow Group 8D. Under surface: petals of the external rows are Red-Purple Group 67B; all other more internal petals are a color between Red-Purple Group 68A and Red-Purple Group 68B. Color of the open flower: Basal spot on upper surface: Yellow-White Group 158D. Upper surface: petals of the external rows are Red-Purple Group 67A; all other more internal petals are Red-Purple Group 68A. Basal spot on under surface: Yellow-White Group 158D. Under surface of the flower: petals of the external rows are Red-Purple Group 67A; all other more internal petals are Red-Purple Group 68A. Anthers: approximately 230 on average, length is less than 0.1 cm, width is less than 0.1 cm, coloration is Green Group 138A in the center and Orange Group 25B on the edges, and arrangement is regular around styles. Filaments: length is approximately 0.2 cm; width is approximately 0.1 cm; and coloration is Green Group 138A slightly suffused with Orange-Red Group 35D. Styles: length is approximately 0.9 cm, coloration is White Group 155D more or less suffused with near Red-Purple Group 63D towards the stigmas, and number is approximately 220 on average. Stigmas: length is approximately 0.1 cm on average and coloration is Yellow Group 6D. Pollen:

medium quantity; color Orange Group 24A. Hips: present but rare; length is approximately 1.5 cm on average; width is approximately 1.5 cm on average; color is Yellow-Green Group 146A suffused with near Greyed-Purple Group 185A; and shape is rounded.

Development:

*Vegetation*.—Medium.

*Blossoming*.—Early in the season, abundant and nearly continuous to fall in France; typically mid-April to first frosts in France.

*Resistance to diseases*.—Good resistance for black spot (*Diplocarpon rosae*).

*Hardiness*.—Tested from Zones 5 to 9.

The new 'MEILEHAGAN' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Hybrid Tea rose plant named 'MEILEHAGAN' characterized by the following combination of characteristics:

(a) forms elegant peony shaped blossoms, (b) displays pink colored flowers, and (c) exhibits dark green colored glossy foliage;

substantially as herein shown and described.

* * * * *

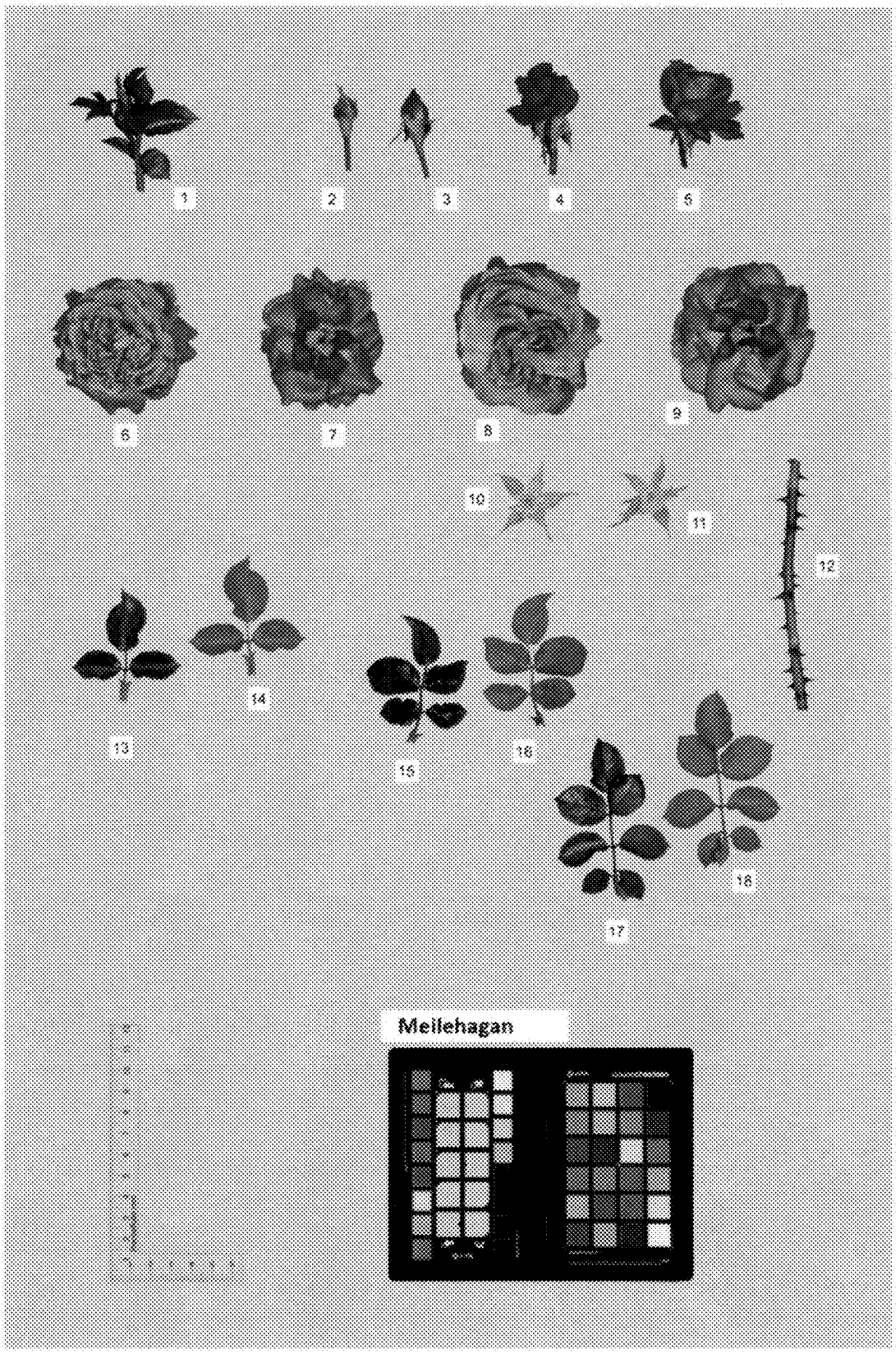
1
2
3
4
5
6
7
8
9
10
11
12
13
14
15
16
17
18
Meilehagan